United States Patent
Tamura

(10) Patent No.: US 9,867,590 B2
(45) Date of Patent: Jan. 16, 2018

(54) PHOTON-COUNTING CT APPARATUS

(71) Applicant: Toshiba Medical Systems Corporation, Otawara-shi (JP)

(72) Inventor: Emi Tamura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 309 days.

(21) Appl. No.: 14/633,690

(22) Filed: Feb. 27, 2015

(65) Prior Publication Data

US 2015/0250444 A1  Sep. 10, 2015

(30) Foreign Application Priority Data

Mar. 5, 2014 (JP) .................. 2014-043146

(51) Int. Cl.
*A61B 6/03* (2006.01)
*H01J 35/10* (2006.01)
(Continued)

(52) U.S. Cl.
CPC .............. *A61B 6/585* (2013.01); *A61B 6/032* (2013.01); *A61B 6/4021* (2013.01); *A61B 6/4035* (2013.01); *A61B 6/4233* (2013.01); *A61B 6/4241* (2013.01); *A61B 6/482* (2013.01); *G01D 18/00* (2013.01); *G01D 18/002* (2013.01); *G01D 18/004* (2013.01); *G01D 18/006* (2013.01); *H01J 35/10* (2013.01); *H01J 35/14* (2013.01); *H01J 35/24* (2013.01); *H01J 35/30* (2013.01); *H01J 35/305* (2013.01); *H01J 2235/081* (2013.01); *H01J 2235/086* (2013.01)

(58) Field of Classification Search
CPC ..... A61B 6/032; A61B 6/4021; A61B 6/4035; A61B 6/4233; A61B 6/4241; A61B 6/482; A61B 6/585; H01J 35/10; H01J 35/14; H01J 35/24; H01J 35/30; H01J 35/305; G01D 18/00; G01D 18/002; G01D 18/004; G01D 18/006
USPC ................ 378/16, 19, 98.9, 98.11, 125, 144, 378/156–159, 124, 137, 207
See application file for complete search history.

(56) References Cited

U.S. PATENT DOCUMENTS 3,610,984 A * 10/1971 Seki ........................ H01J 35/10
  378/115
4,571,286 A * 2/1986 Penato .................. C04B 41/009
  205/118
(Continued)

FOREIGN PATENT DOCUMENTS

JP  2002-195961 A  7/2002
JP  2006-155925 A  6/2006

*Primary Examiner* — Allen C. Ho
(74) *Attorney, Agent, or Firm* — Oblon, McClelland, Maier & Neustadt, L.L.P.

(57) ABSTRACT

According to one embodiment, a photon counting CT apparatus includes an X-ray source, a photon counting CT detector, and a calibration unit. The X-ray source includes a cathode configured to generate electrons and an anode including a plurality of targets configured to generate a plurality of characteristic X-rays having different energies. The photon counting CT detector detects X-ray photons generated by the X-ray source. The calibration unit calibrates the gain of the photon counting CT detector based on the correspondence relationship between the photon energies of the plurality of characteristic X-rays and outputs from the photon counting CT detector.

16 Claims, 10 Drawing Sheets

(51) Int. Cl.
*H01J 35/14* (2006.01)
*H01J 35/24* (2006.01)
*H01J 35/30* (2006.01)
*A61B 6/00* (2006.01)
*G01D 18/00* (2006.01)

(56) References Cited

U.S. PATENT DOCUMENTS

| | | | | |
|---|---|---|---|---|
| 4,799,250 A * | 1/1989 | Penato | H01J 35/108 | 378/125 |
| 5,155,365 A * | 10/1992 | Cann | A61B 6/4241 | 250/363.02 |
| 5,204,888 A * | 4/1993 | Tamegai | A61B 6/4035 | 378/156 |
| 5,247,559 A * | 9/1993 | Ohtsuchi | A61B 6/4035 | 378/53 |
| 5,511,105 A * | 4/1996 | Knott | H01J 35/24 | 378/125 |
| 5,570,403 A * | 10/1996 | Yamazaki | A61B 6/032 | 378/19 |
| 5,907,592 A * | 5/1999 | Levinson | H01J 35/10 | 378/144 |
| 5,943,388 A * | 8/1999 | Tümer | G01V 5/0041 | 378/98.11 |
| 6,226,352 B1 * | 5/2001 | Salb | A61B 6/4035 | 378/143 |
| 6,246,747 B1 * | 6/2001 | Wear | G01N 23/083 | 378/98.11 |
| 6,487,274 B2 * | 11/2002 | Bertsche | A61N 5/10 | 378/124 |
| 6,553,096 B1 * | 4/2003 | Zhou | A61B 6/4488 | 378/122 |
| 6,560,315 B1 * | 5/2003 | Price | H01J 35/10 | 378/125 |
| 6,574,302 B2 * | 6/2003 | Adriaansz | A61B 6/032 | 378/18 |
| 6,950,492 B2 * | 9/2005 | Besson | A61B 6/508 | 378/16 |
| 6,987,833 B2 * | 1/2006 | Du | A61B 6/032 | 378/5 |
| 7,085,351 B2 * | 8/2006 | Lu | A61B 6/4021 | 315/169.3 |
| 7,120,222 B2 * | 10/2006 | Hoffman | A61B 6/032 | 378/124 |
| 7,149,278 B2 * | 12/2006 | Arenson | A61B 6/4241 | 378/19 |
| 7,187,756 B2 * | 3/2007 | Gohno | G01N 23/046 | 378/124 |
| 7,209,536 B2 * | 4/2007 | Walter | A61B 6/032 | 378/5 |
| 7,263,167 B2 * | 8/2007 | Walter | A61B 6/032 | 378/116 |
| 7,483,518 B2 * | 1/2009 | Hamill | G21K 1/10 | 378/119 |
| 7,532,703 B2 * | 5/2009 | Du | A61B 6/032 | 378/116 |
| 7,573,040 B2 * | 8/2009 | Tkaczyk | G01T 1/249 | 250/370.09 |
| 7,613,274 B2 * | 11/2009 | Tkaczyk | A61B 6/032 | 378/19 |
| 7,634,061 B1 * | 12/2009 | Tümer | G01T 1/247 | 378/62 |
| 7,636,413 B2 * | 12/2009 | Toth | A61B 6/032 | 378/157 |
| 7,649,981 B2 * | 1/2010 | Seppi | A61B 6/032 | 378/124 |
| 7,696,483 B2 * | 4/2010 | Tkaczyk | G01T 1/171 | 250/370.06 |
| 7,792,241 B2 * | 9/2010 | Wu | H01J 35/045 | 378/114 |
| 7,826,587 B1 * | 11/2010 | Langan | A61B 6/032 | 378/16 |
| 7,829,860 B2 * | 11/2010 | Nygard | G01T 1/2018 | 250/366 |
| 7,852,979 B2 * | 12/2010 | Edic | A61B 6/032 | 378/134 |
| 7,868,665 B2 * | 1/2011 | Tümer | H03F 3/087 | 327/509 |
| 7,869,571 B2 * | 1/2011 | Hsieh | A61B 6/032 | 378/124 |
| 7,869,862 B2 * | 1/2011 | Seppi | A61B 6/032 | 600/420 |
| 7,943,907 B2 * | 5/2011 | Eversmann | G01T 1/17 | 250/395 |
| 8,000,434 B2 * | 8/2011 | Ziegler | G01T 1/2985 | 378/4 |
| 8,213,566 B2 * | 7/2012 | Roessl | A61B 5/4869 | 378/5 |
| 8,299,440 B2 * | 10/2012 | Wainer | G01T 1/1647 | 250/363.04 |
| 8,338,791 B2 * | 12/2012 | Proksa | G01T 1/171 | 250/369 |
| 8,422,636 B2 * | 4/2013 | Greenberg | G01T 1/29 | 378/5 |
| 8,442,184 B2 * | 5/2013 | Forthmann | A61B 6/032 | 378/5 |
| 8,483,361 B2 * | 7/2013 | Sainath | A61B 6/027 | 378/125 |
| 8,488,854 B2 * | 7/2013 | Arenson | G06T 11/005 | 378/1 |
| 8,525,122 B2 * | 9/2013 | Chappo | A61B 6/00 | 250/370.11 |
| 8,653,471 B2 * | 2/2014 | Proksa | A61B 6/032 | 250/363.01 |
| 8,913,711 B2 * | 12/2014 | Moriyasu | A61B 6/03 | 378/4 |
| 8,929,508 B1 * | 1/2015 | Alvarez | G01N 23/087 | 378/18 |
| 8,965,095 B2 * | 2/2015 | Zou | G06T 11/005 | 378/4 |
| 9,020,092 B2 * | 4/2015 | Wang | A61B 6/583 | 378/5 |
| 9,052,266 B2 * | 6/2015 | Miyazaki | A61B 6/4241 | |
| 9,149,241 B2 * | 10/2015 | Kim | A61B 6/482 | |
| 9,155,516 B2 * | 10/2015 | Wang | A61B 6/4241 | |
| 9,164,183 B2 * | 10/2015 | Kraft | G01T 1/40 | |
| 9,198,629 B2 * | 12/2015 | Wiedmann | H01J 35/10 | |
| 9,208,585 B2 * | 12/2015 | Leng | A61B 6/032 | |
| 9,254,109 B2 * | 2/2016 | Becker | A61B 6/032 | |
| 9,268,035 B2 * | 2/2016 | Herrmann | G01T 1/17 | |
| 9,310,495 B2 * | 4/2016 | Spartiotis | G01T 1/247 | |
| 9,316,745 B2 * | 4/2016 | Noshi | G01T 1/17 | |
| 9,335,424 B2 * | 5/2016 | Herrmann | G01T 1/171 | |
| 9,354,331 B2 * | 5/2016 | Sagoh | A61B 6/032 | |
| 9,417,339 B2 * | 8/2016 | Spahn | G01T 1/247 | |
| 9,418,816 B2 * | 8/2016 | Kondo | A61B 6/032 | |
| 9,476,993 B2 * | 10/2016 | Wang | G01T 1/17 | |
| 9,504,438 B2 * | 11/2016 | Proksa | G01T 1/24 | |
| 9,517,045 B2 * | 12/2016 | Kang | G01N 23/087 | |
| 9,535,167 B2 * | 1/2017 | Proksa | G01T 1/171 | |
| 9,693,743 B2 * | 7/2017 | Arakita | G01T 1/1606 | |
| 9,706,967 B2 * | 7/2017 | Wang | A61B 6/4241 | |
| 9,759,822 B2 * | 9/2017 | Daerr | G01T 1/247 | |

* cited by examiner

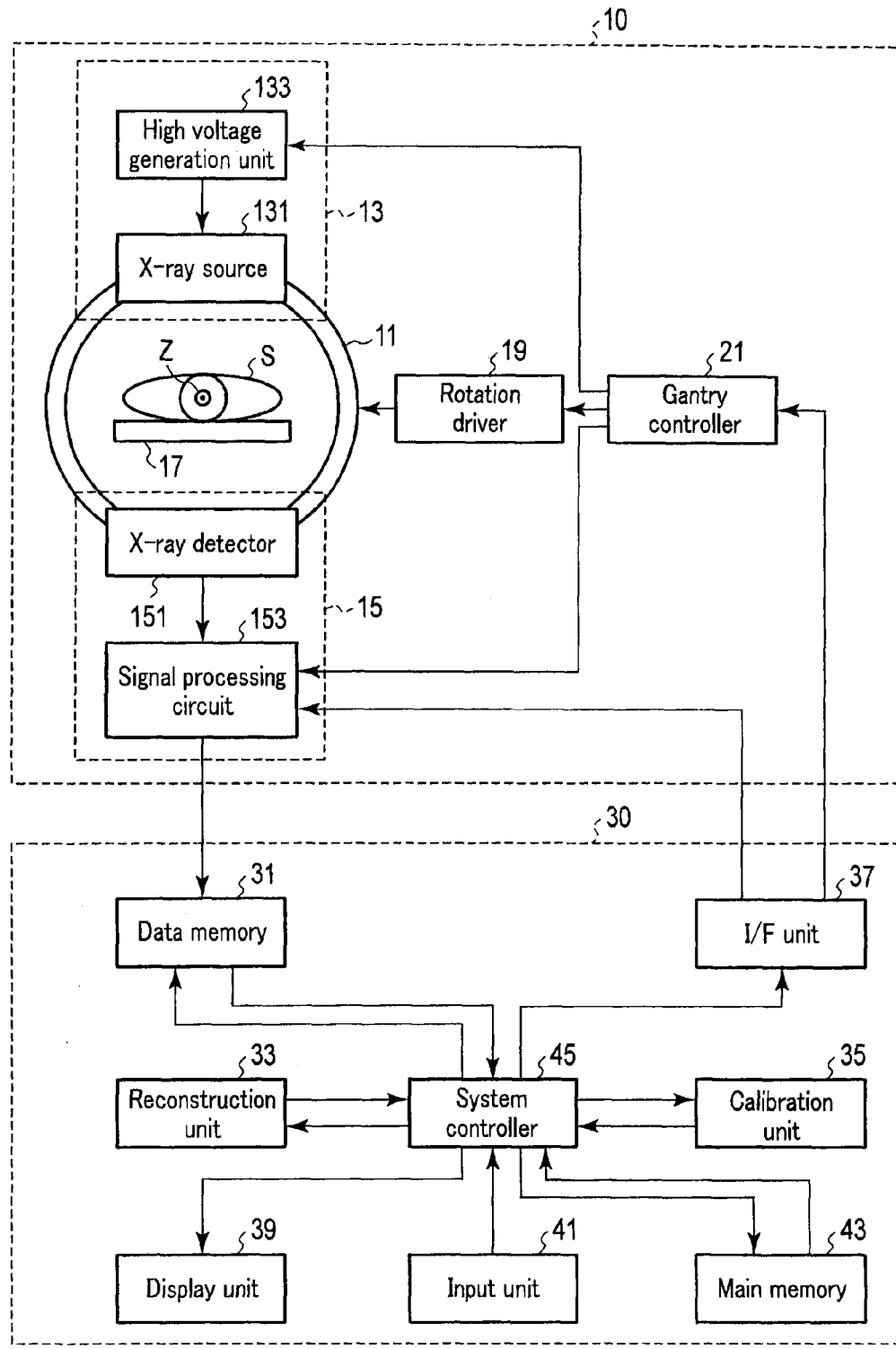
F I G. 1

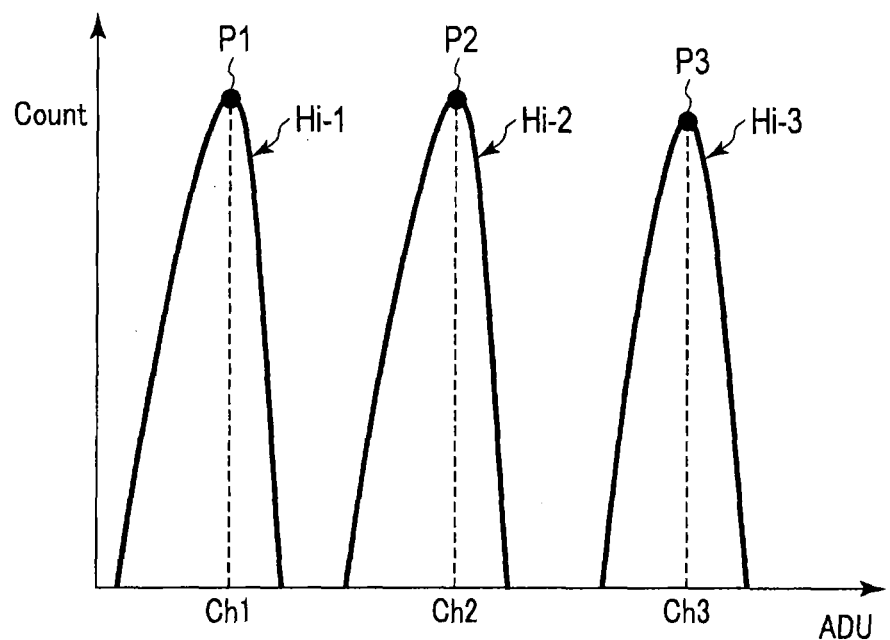
F I G. 7
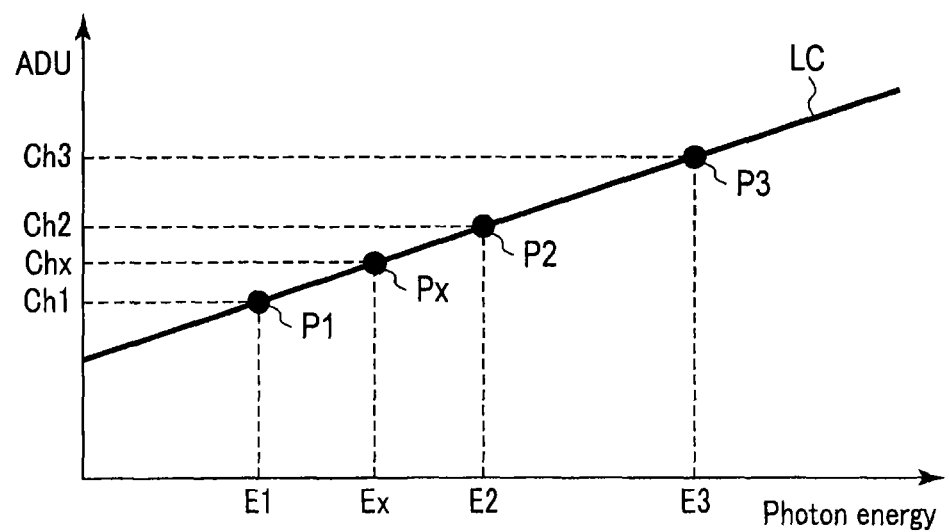
F I G. 8

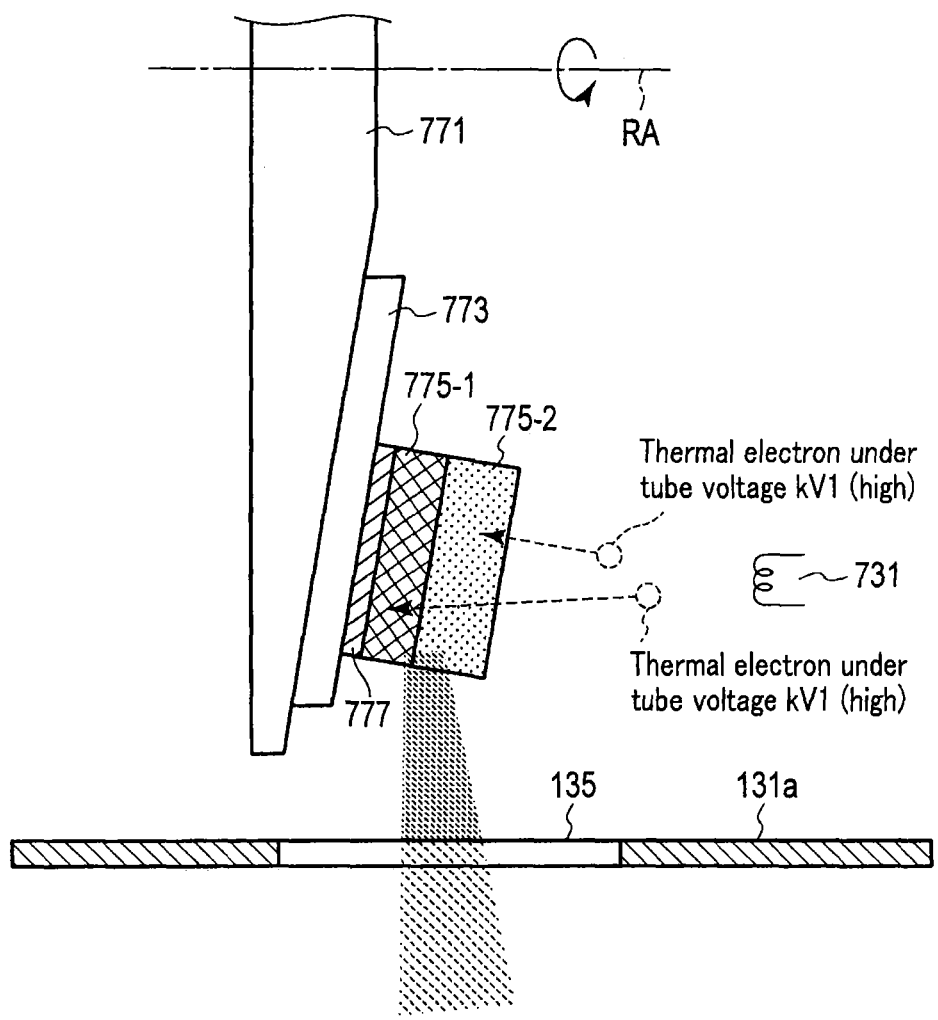
F I G. 10

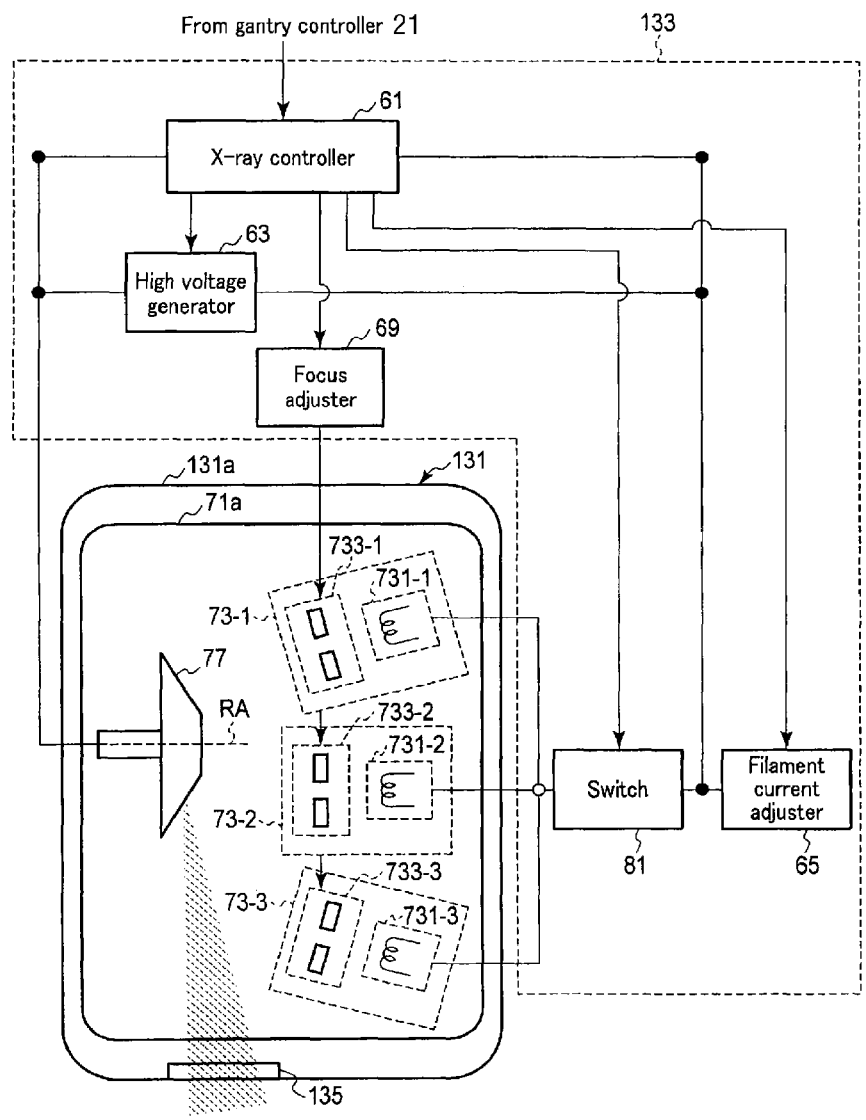
F I G. 12

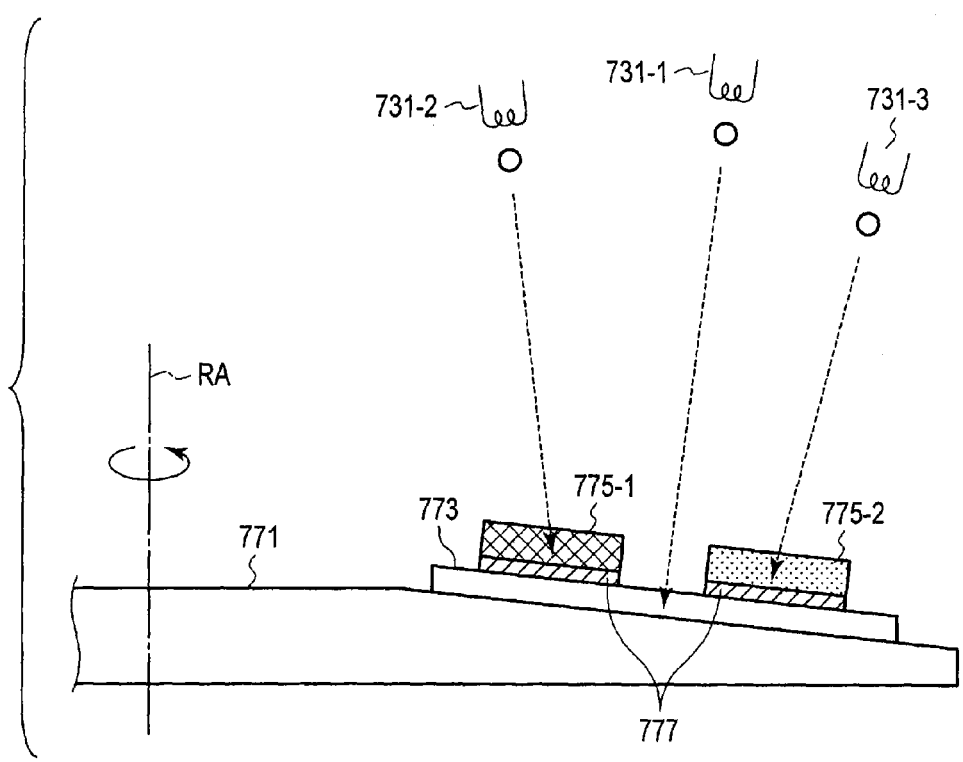
F I G. 13

PHOTON-COUNTING CT APPARATUS

CROSS-REFERENCE TO RELATED APPLICATIONS

This application is based upon and claims the benefit of priority from the prior Japanese Patent Application No. 2014-043146, filed Mar. 5, 2014 the entire contents of which are incorporated herein by reference.

FIELD

Embodiments described herein relate generally to a photon counting CT apparatus.

BACKGROUND

An X-ray computed tomography apparatus uses air, various types of phantoms, and the like for the calibration of a detector. In general, an RI (Radioactive Isotope) is often used for the calibration of the gain of the detector. In order to calibrate a photon counting CT detector by using an RI, however, it is necessary to use an RI having a radioactivity of 100 MBq or more. This is practically difficult. A detector varies in properties depending on external environments such as temperatures. In addition, in photon counting CT, since data is processed for each energy bin having a predetermined energy width, it is necessary to accurately calibrate the gain of a device.

BRIEF DESCRIPTION OF THE DRAWING

FIG. 1 is a block diagram showing the arrangement of a photon counting CT apparatus according to an embodiment;

FIG. 7 is a graph schematically showing the histograms of X-ray photons detected by a photon counting CT detector in FIG. 1;

FIG. 8 is a graph showing the relationship between the central channels and the photon energies according to FIG. 7;

FIG. 10 is a view for explaining an example of the operation of an X-ray controller according to modification 2, and schematically showing an example of generating X-rays from the first calibration target;

FIG. 12 is a block diagram schematically showing the calibration of an X-ray source apparatus according to modification 3; and FIG. 13 is a view for explaining an example of the operation of an X-ray controller according to modification 3.

DETAILED DESCRIPTION

Figure 2:
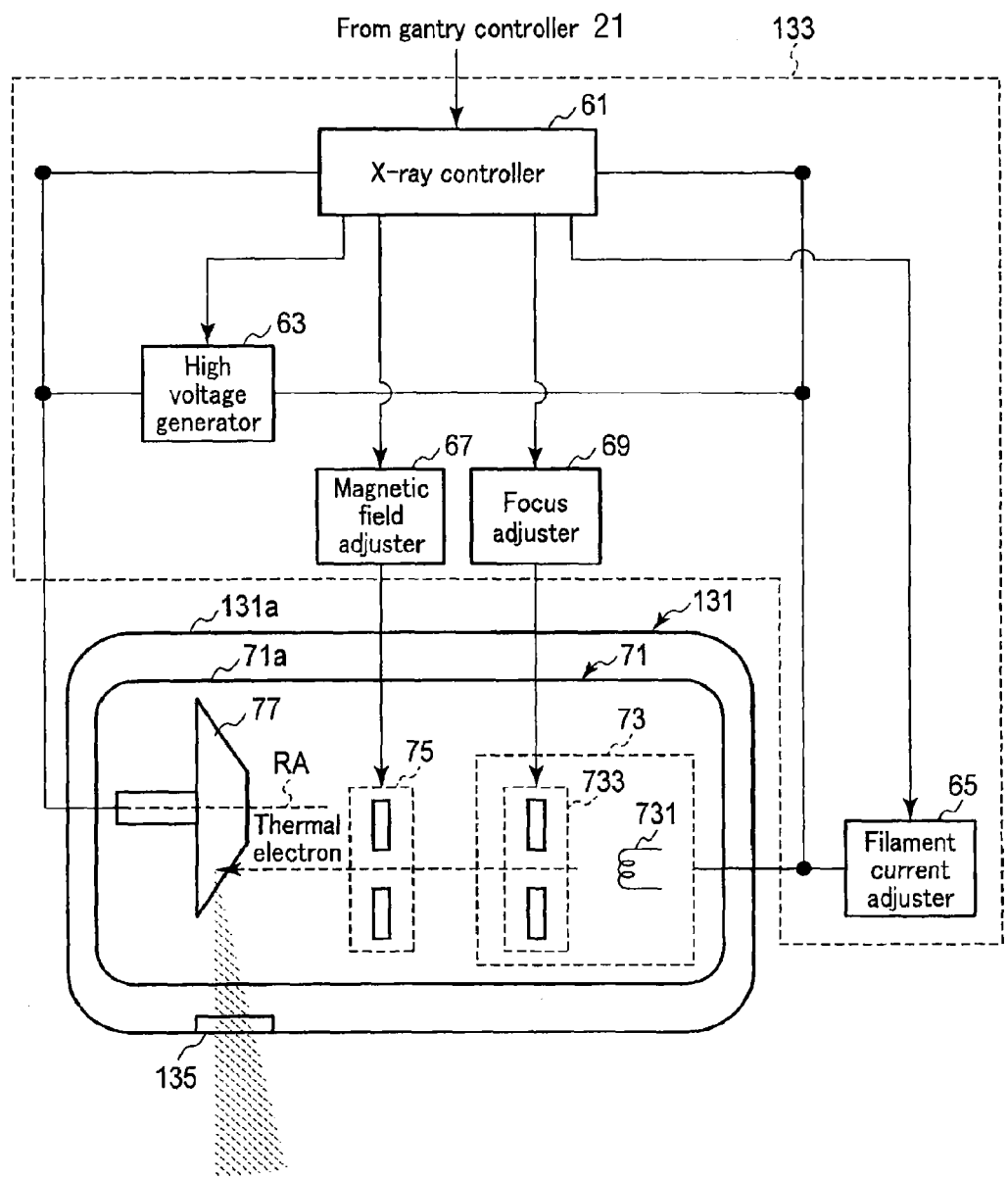
FIG. 2 is a block diagram schematically showing the arrangement of an X-ray source apparatus in FIG. 1.

In general, according to one embodiment, a photon counting CT apparatus includes an X-ray source, a photon counting CT detector, and a calibration unit. The X-ray source includes a cathode configured to generate electrons and an anode including a plurality of targets configured to generate a plurality of characteristic X-rays having different energies. The photon counting CT detector detects X-ray photons generated by the X-ray source. The calibration unit calibrates the gain of the photon counting CT detector based on the correspondence relationship between the photon energies of the plurality of characteristic X-rays and outputs from the photon counting CT detector.

The photon counting CT apparatus according to this embodiment will be described below with reference to the accompanying drawing.

FIG. 1 is a block diagram showing the arrangement of the photon counting CT apparatus according to this embodiment. As shown in FIG. 1, the photon counting CT apparatus according to the embodiment includes a gantry 10 and a console 30. The gantry 10 supports a rotating frame 11 having a cylindrical shape so as to make it rotatable about a rotation axis Z. An X-ray source apparatus 13 and a photon counting CT detector 15 are mounted on the rotating frame 11 so as to face each other through the rotation axis Z. An FOV (Field Of View) is set in the bore of the rotating frame 11. A top 17 is inserted into the bore of the rotating frame 11. A subject S is placed on the top 17. The top 17 is positioned such that an imaging region of the subject S placed on the top 17 is included in the FOV. The rotating frame 11 rotates about the rotation axis Z at a constant angular velocity upon receiving power from a rotation driver 19. The rotation driver 19 generates power for rotating the rotating frame 11 under the control of a gantry controller 21.

The X-ray source apparatus 13 includes an X-ray source 131 and a high voltage generation unit 133. The X-ray source 131 is connected to the high voltage generation unit 133. The high voltage generation unit 133 applies a high voltage and supplies a filament current to the X-ray source 131 under the control of the gantry controller 21. The X-ray source 131 according to this embodiment includes a cathode which can generate electrons and an anode having a structure capable of generating characteristic X-rays having different energies.

FIG. 2 is a block diagram schematically showing the arrangement of the X-ray source apparatus 13 shown in FIG. 1 according to this embodiment. As shown in FIG. 2, the X-ray source apparatus includes the X-ray source 131 and the high voltage generation unit 133. The high voltage generation unit 133 includes an X-ray controller 61, a high voltage generator 63, a filament current adjuster 65, a magnetic field adjuster 67, and a focus adjuster 69.

The X-ray source 131 includes an X-ray tube container 131a. The X-ray tube container 131a is filled with an insulating oil. The X-ray tube container 131a accommodates an X-ray tube 71. The X-ray tube 71 includes a housing 71a. A vacuum is maintained in the housing 71a. The housing 71a is formed from, for example, a glass or metal material. The housing 71a incorporates a cathode 73, a magnetic field generator 75, and an anode 77. The cathode 73 includes a filament 731 and a focusing electrode 733. The cathode 73 is connected to the high voltage generator 63 and the filament current adjuster 65 via a cable or the like. The high voltage generator 63 applies a tube voltage between the cathode 73 and the anode 77 under the control of the X-ray controller 61. The filament current adjuster 65 adjusts the filament current to be supplied to the filament 731 under the control of the X-ray controller 61. Upon receiving the filament current, the filament 731 generates heat and emits thermal electrons. The tube voltage applied between the filament 731 and the anode 77 causes the emitted thermal electrons to fly and collide with the anode 77. The colliding range of thermal electrons with respect to the anode 77 is called a focus. The anode 77 is an electrode having a disk-like shape. The anode 77 is provided so as to be rotatable about a rotation axis (to be referred to as an anode rotation axis hereinafter) RA. Upon receiving the thermal electrons from the filament 731, the anode 77 emits X-rays toward a window 135 provided in the X-ray tube container 131a.

The focusing electrode 733 for focusing the thermal electrons emitted from the filament 731 is provided between the filament 731 and the anode 77. The focusing electrode 733 is connected to the focus adjuster 69. The focus adjuster 69 applies a voltage (focusing electrode voltage) to the focusing electrode 733 under the control of the X-ray controller 61. The thermal electrons emitted from the filament 731 are focused into a beam by a focusing electrode voltage. The size of the focus formed on the anode 77 changes in accordance with the focusing electrode voltage. The focus adjuster 69 adjusts the focusing electrode voltage under the control of the X-ray controller 61. The magnetic field generator 75 is provided between the focusing electrode 733 and the anode 77. The magnetic field generator 75 is connected to the magnetic field adjuster 67. The magnetic field adjuster 67 applies a voltage (deflecting voltage) to the magnetic field generator 75 under the control of the X-ray controller 61. Upon receiving the applied deflecting voltage, the magnetic field generator 75 generates a magnetic field according to the principle of electromagnetic induction. The magnetic field adjuster 67 can adjust the intensity of the magnetic field generated by the magnetic field generator 75 under the control of the X-ray controller 61. The magnetic field generated by the magnetic field generator 75 deflects the path of thermal electrons emitted from the filament 731. The position of the focus formed on the anode 77 is changed by deflecting the path of thermal electrons.

The X-ray controller 61 synchronously controls the high voltage generator 63, the filament current adjuster 65, the magnetic field adjuster 67, and the focus adjuster 69 under the control of the gantry controller 21. The X-ray controller 61 controls the high voltage generator 63, the filament current adjuster 65, the magnetic field adjuster 67, and the focus adjuster 69 such that the anode 77 generates X-rays for patient imaging with respect to the subject S as a target in a photon counting CT imaging mode (to be referred to as a patient imaging mode hereinafter), and the anode 77 generates X-rays for calibration in a calibration mode.

As shown in FIG. 1, the photon counting CT detector 15 detects the X-rays generated by the X-ray source apparatus 13 by the X-ray photons. More specifically, in the patient imaging mode, the photon counting CT detector 15 acquires count data expressing the detected count of X-ray photons in a plurality of energy bins. More specifically, the photon counting CT detector 15 includes an X-ray detector 151 and a signal processing circuit 153.

The X-ray detector 151 detects the X-ray photons generated by the X-ray source 131. The X-ray detector 151 is equipped with a plurality of two dimensionally arrayed detection elements. The X-ray detector 151 is typically implemented by a direct detection type semiconductor detector. Each X-ray detection element detects an X-ray photon from the X-ray source 131 and generates an electrical pulse (electrical signal) in accordance with the energy of the detected X-ray photon. More specifically, each X-ray detection element is formed from a semiconductor diode having electrodes mounted on the two ends of a semiconductor. An X-ray photon entering the semiconductor is converted into electron hole pairs. The number of electron hole pairs generated by the incidence of one X-ray photon depends on the energy of the incident X-ray photon. Electrons and holes are attracted by the pair of electrodes formed on the two ends of the semiconductor. One pair of electrodes generate an electrical pulse having a peak value corresponding to an electron hole pair charge. One electrical pulse has a peak value corresponding to the energy of an incident X-ray photon. As a semiconductor material according to this embodiment, it is preferable to use a semiconductor material having a relatively large atomic number which can efficiently convert an X-ray photon into hole electron pairs. As a semiconductor material suitable for photon counting CT, for example, CdTe or CdZnTe is known. Note that the X-ray detector 151 according to this embodiment is not limited to a direct detection type semiconductor detector and may be an indirect detection type detector. As the indirect detection type X-ray detector 151, a detector of a type combining a scintillator and an optical sensor can be used. Note that the optical sensor may be, for example, SiPM (Silicon Photo-Multipliers).

The signal processing circuit 153 acquires count data expressing the count of X-ray photons detected by the X-ray detector 151 for each of a plurality of energy bins under the control of the gantry controller 21. The signal processing circuit 153 is equipped with readout channels corresponding to the number of detector pixels of the X-ray detector 151. These readout channels are mounted in parallel on an integrated circuit such as ASIC (Application Specific Integrated Circuits).

Figure 3:
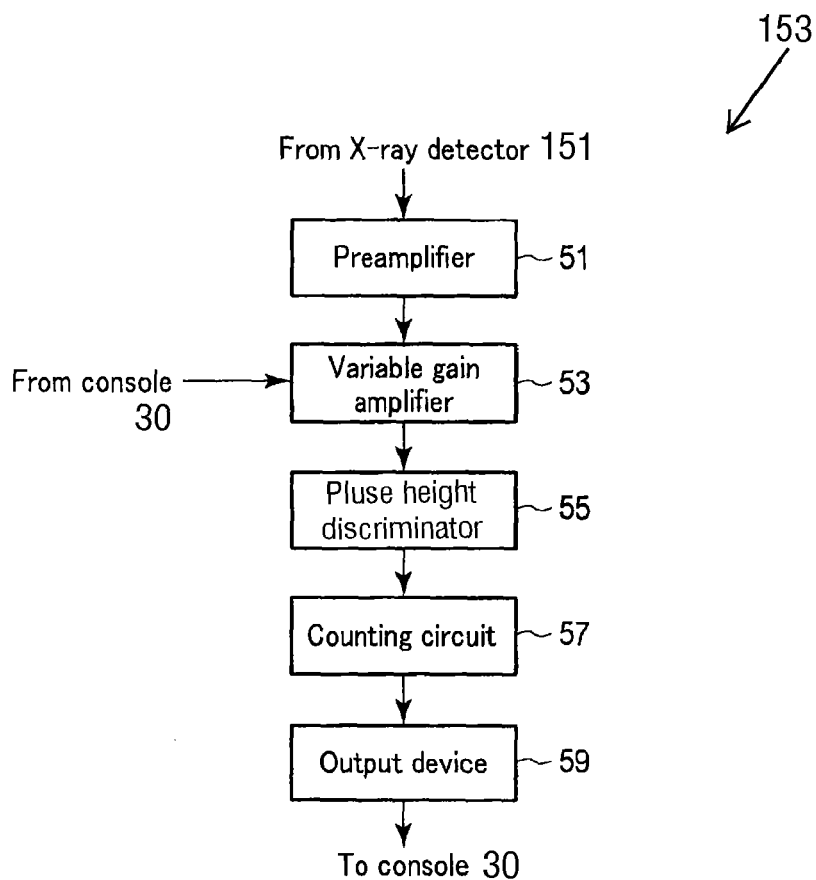
FIG. 3 is a block diagram showing the arrangement of a portion, of a signal processing circuit in FIG. 1, which corresponds to one channel.

FIG. 3 is a block diagram showing the arrangement of a portion, of the signal processing circuit 153, which corresponds to one channel. As shown in FIG. 3, the signal processing circuit 153 includes a preamplifier 51, a variable gain amplifier 53, a pulse height discriminator 55, a counting circuit 57, and an output device 59. The preamplifier 51 amplifies an electrical signal from the X-ray detector 151 with a constant gain (amplification ratio). The variable gain amplifier 53 amplifies an electrical signal from the preamplifier 51 with a variable gain (amplification ratio). A calibration unit 35 included in the console 30 adjusts a variable gain. The pulse height discriminator 55 discriminates the energy bins of electrical signals from the variable gain amplifier 53. More specifically, the pulse height discriminator 55 discriminates an energy bin, of a plurality of predetermined energy bins, to which each X-ray photon detected by the X-ray detector 151 belongs by comparing the peak value of an electrical signal from the variable gain amplifier 53, which originates from the X-ray photon, with a threshold. The pulse height discriminator 55 outputs an electrical pulse (to be referred to as a discrimination signal hereinafter) corresponding to the type of energy bin to which the X-ray photon belongs. The counting circuit 57 counts the X-ray photons detected by the X-ray detector 151 for each of the plurality of energy bins. More specifically, the counting circuit 57 counts discrimination signals from the pulse height discriminator 55 concerning each of the plurality of energy bins for each view, and generates count data expressing the count of X-ray photons detected by the X-ray detector 151. An energy bin is defined by an ADU (Analog to Digital Unit). In other words, count data is data expressing a count for each of a plurality of ADUs. The output device 59 transmits the count data to the console 30.

As shown in FIG. 1, the gantry controller 21 comprehensively controls the respective types of units mounted on the gantry 10. The gantry controller 21 includes, as hardware resources, an arithmetic device (processor) such as a CPU (Central Processing Unit) or MPU (Micro Processing Unit) and storage devices (memories) such as a ROM (Read Only Memory) and a RAM (Random Access Memory). More specifically, the gantry controller 21 switches between control modes for the high voltage generation unit 133, the signal processing circuit 153, and the rotation driver 19 in accordance with the type of patient imaging mode and calibration mode designated by the console 30. More specifically, the gantry controller 21 switches between the control modes depending on the patient imaging mode or the calibration mode. In the patient imaging mode, the rotation driver 19 rotates at a constant angular velocity under the control of the gantry controller 21. The high voltage generation unit 133 applies a high voltage (tube voltage) corresponding to a set tube voltage value to the X-ray source 131 and supplies a filament current to the X-ray source 131 under the control of the gantry controller 21. The signal processing circuit 153 acquires count data concerning each of a plurality of energy bins for each view in synchronism with an X-ray exposure timing under the control of the gantry controller 21. In the calibration mode, the gantry controller 21 controls the high voltage generation unit 133 to cause the X-ray source 131 to generate a plurality of characteristic X-rays having different energies. The signal processing circuit 153 acquires count data concerning the plurality of characteristic X-rays. Note that a plurality of characteristic X-rays may be generated by the X-ray source 131 simultaneously or at different timings.

The console 30 includes a computer including a Data memory 31, a reconstruction unit 33, the calibration unit 35, an I/F unit 37, a display unit 39, an input unit 41, a Main memory 43, and a system controller 45.

The Data memory 31 is a storage device such as an HDD (Hard Disk Drive), SSD (Solid State Drive), or integrated circuit storage device. The Data memory 31 stores count data concerning a plurality of energy bins transmitted from the gantry 10.

The reconstruction unit 33 includes, as hardware resources, an arithmetic device (processor) such as a CPU or MPU and storage devices (memories) such as a ROM and a RAM. The reconstruction unit 33 reconstructs a photon counting CT image concerning a visualization target energy bin based on the count data stored in the Data memory 31. As this image reconstruction algorithm, it is possible to use an existing image reconstruction algorithm such as an analytical image reconstruction method, e.g., an FBP (Filtered Back Projection) method or CBP (Convolution Back Projection) method, or a statistical image reconstruction method, e.g., an ML-EM (Maximum Likelihood Expectation Maximum) method or OS-EM (Ordered Subset Expectation Maximization) method.

The calibration unit 35 includes, as hardware resources, an arithmetic device (processor) such as a CPU or MPU and storage devices (memories) such as a ROM and a RAM. The calibration unit 35 calibrates the gain of the photon counting CT detector 15 based on the relationship between the photon energies of a plurality of characteristic X-rays and outputs from the photon counting CT detector 15. More specifically, the calibration unit 35 calibrates the gain of the photon counting CT detector 15 based on the correspondence relationship between the photon energy of each of a plurality of characteristic X-rays for calibration and the energy bin to which the photon energy of the characteristic X-ray theoretically belongs. The calibration target gain of the calibration unit 35 indicates the correspondence relationship between an X-ray energy value and an output value from the photon counting CT detector 15.

The I/F unit 37 is an interface for communication between the console 30 and the gantry 10. For example, the I/F unit 37 supplies an imaging start signal, an imaging stop signal, and the like from the system controller 45 to the gantry 10. In addition, the I/F unit 37 supplies data representing the type of imaging mode such as the patient imaging mode or calibration mode.

The display unit 39 displays various types of information such as a photon counting CT image on a display device. As the display device, it is possible to use, for example, a CRT display, liquid crystal display, organic EL display, or plasma display, as needed.

The input unit 41 accepts various types of commands and information inputs from the user via an input device. As the input device, it is possible to use a keyboard, a mouse, various types of switches, and the like.

The Main memory 43 is a storage device which stores various types of information. For example, the Main memory 43 stores a calibration program for the photon counting CT detector 15 according to this embodiment, an imaging program for the photon counting CT apparatus, and the like.

The system controller 45 includes, as hardware resources, an arithmetic device (processor) such as a CPU or MPU and storage devices (memories) such as a ROM and a RAM. The system controller 45 functions as the main unit of the photon counting CT apparatus according to this embodiment. The system controller 45 reads out the calibration program according to the embodiment from the Main memory 43, and controls the respective types of constituent elements in accordance with the calibration program. With this operation, the photon counting CT detector 15 is calibrated. In addition, the system controller 45 reads out the imaging program according to the embodiment from the Main memory 43, and controls the respective types of constituent elements in accordance with the imaging program. With this operation, photon counting CT imaging is performed.

An example of the operation of the photon counting CT apparatus according to this embodiment will be described below.

Figure 4:
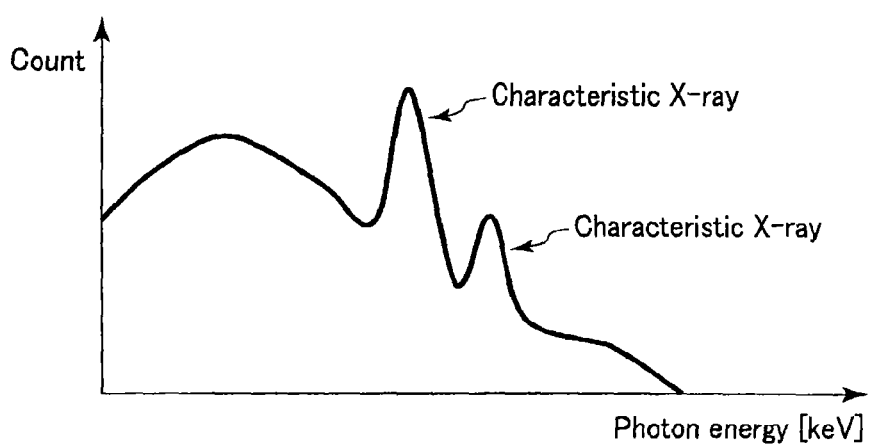
FIG. 4 is a graph showing the energy spectrum of X-rays originating from a given element.

The use of characteristic X-rays at the time of gain calibration will be described below. FIG. 4 is a graph showing the energy spectrum of X-rays originating from a given element. Referring to FIG. 4, the ordinate is defined as the count, and the abscissa is defined as the photon energy [keV]. As shown in FIG. 4, the energy spectrum of X-rays has an emission line structure originating from characteristic X-rays. The characteristic X-rays have a photon energy unique to the element as an X-ray source.

A general X-ray computed tomography apparatus performs calibration by using a radioactive isotope which emits a single or a plurality of known characteristic X-rays (emission lines). However, it is difficult from various viewpoints to incorporate a radioactive isotope in the X-ray computed tomography apparatus. Although it is possible to perform calibration by using characteristic X-rays emitted from an imaging target mounted in an X-ray source, the imaging target is formed from a single element. For this reason, the number of characteristic X-rays emitted from the X-ray source is small, and they are distributed in a narrow energy range. It is therefore impossible to perform accurate gain calibration required for the photon counting CT detector 15.

The photon counting CT apparatus according to this embodiment includes the X-ray source apparatus 13 capable of generating a plurality of characteristic X-rays having different energies, and calibrates the gain of the photon counting CT detector 15 by using a plurality of characteristic X-rays.

Figure 5:
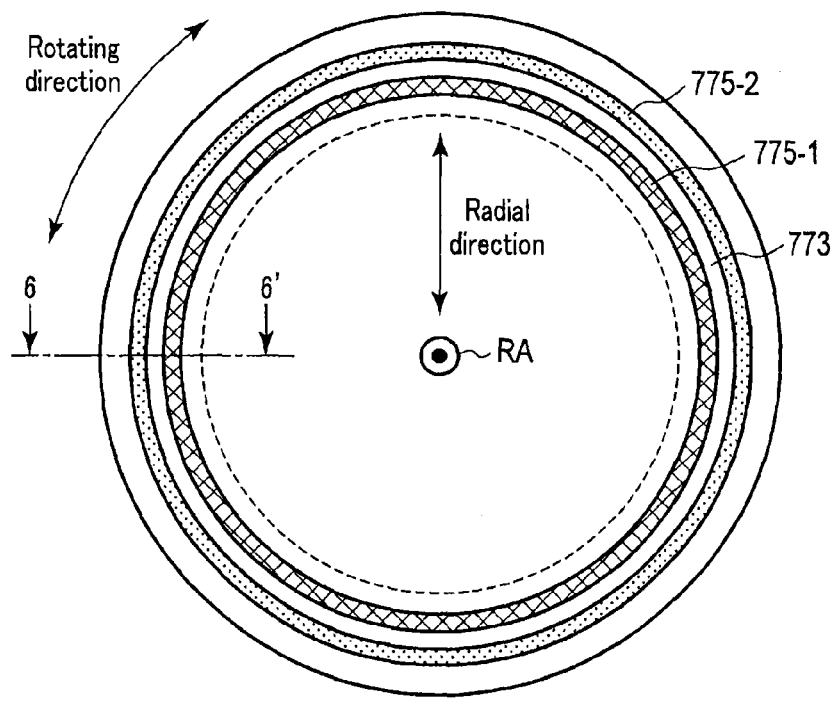
FIG. 5 is a plan view of an anode in FIG. 2.
Figure 6:
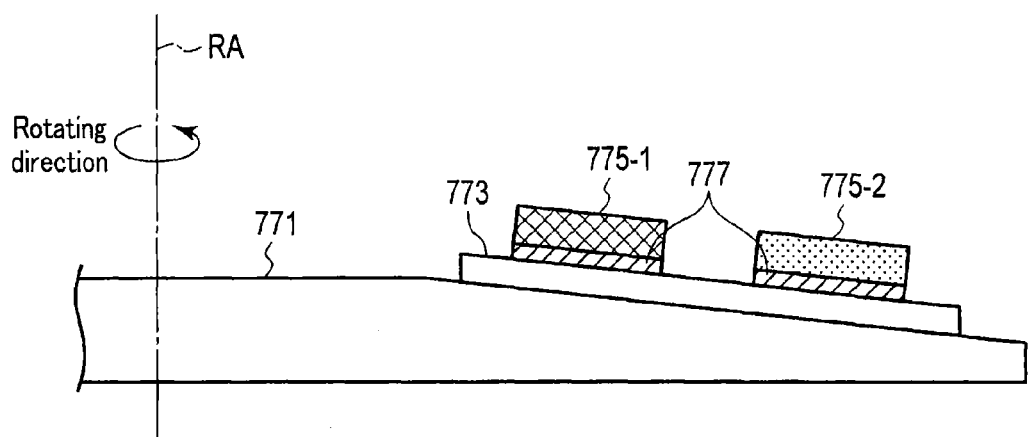
FIG. 6 is a sectional view taken along 6-6' in FIG. 5.

The structure of the anode of the X-ray source apparatus will be described first. FIG. 5 is a plan view of the anode according to this embodiment. FIG. 6 is a sectional view taken along 6 6' in FIG. 5. Note that FIG. 5 is a plan view of the anode viewed from the filament 731. As shown in FIGS. 5 and 6, the anode is provided to be rotatable about the anode rotation axis RA. The anode has a base 771 formed from a metal. An imaging target 773 is provided on the base 771. The imaging target 773 is mainly used in the patient imaging mode. Note that the imaging target 773 may be used in the calibration mode. The imaging target 773 is formed from an element belonging to heavy metal such as tungsten (W) with atomic number of 74 or molybdenum (Mo) with atomic number of 42. A calibration target is provided on the surface of the imaging target 773. The calibration target is mounted on the imaging target 773 by deposition or the like. The calibration target is formed from a single element different in type from that forming the imaging target 773. At least one calibration target may be provided. When arranging a plurality of calibration targets, it is preferable to form them by using different types of elements to enable the generation of characteristic X-rays having different energies. More specifically, the plurality of characteristic X-rays preferably belong to different energy bins. For example, as shown in FIGS. 5 and 6, two calibration targets 775-1 and 775-2 are preferably provided on the imaging target 773. As elements for calibration targets 775-1 and 775-2 according to this embodiment, it is preferable to use, for example, tin (Sn) with atomic number of 50, lead (Pb) with atomic number of 82, and gold (Au) with atomic number of 79.

As shown in FIGS. 5 and 6, the plurality of calibration targets are arranged side by side on the imaging target 773. Each calibration target is preferably formed into an arbitrary shape. For example, as shown in FIG. 6, each calibration target is preferably formed into an annular shape. Forming the calibration target into an annular shape makes it possible to continuously irradiate the same calibration target with thermal electrons while rotating the anode about the anode rotation axis RA. Rotating the anode can reduce a deterioration in the calibration target caused by the collision of thermal electrons. The plurality of calibration targets 775-1 and 775-2 are arrayed in the radial direction of the anode. As shown in FIGS. 5 and 6, the plurality of calibration targets 775-1 and 775-2 may be arranged at intervals from each other. In this case, the imaging target 773 is exposed between the plurality of calibration targets 775-1 and 775-2 to allow thermal electrons to collide with the imaging target 773. Note that the plurality of calibration targets 775-1 and 775-2 may be arranged at short intervals from each other. Even in this case, the imaging target 773 needs to be exposed to allow thermal electrons to collide with the imaging target 773.

Note that the imaging target 773 and the calibration target contain different types of elements, and hence have different melting points. If the imaging target 773 has a higher melting point than each calibration target, the calibration target may be melted by the heat generated by the imaging target 773. For this reason, heat insulators 777 are preferably interposed between the imaging target 773 and the calibration target 775-1 contacting the imaging target 773 and between the imaging target 773 and the calibration target 775-2, respectively. Providing the heat insulators 777 can insulate the calibration targets 775-1 and 775-2 against heat from the imaging target 773 and prevent the calibration targets 775-1 and 775-2 from being melted. As a material for the heat insulators 777, it is preferable to use a material having a higher melting point than the element used for the imaging target 773, e.g., a material containing carbon.

X-ray irradiation from the X-ray source 131 under the control of the X-ray controller 61 will be described below. Assume that in this operation example, an X-ray generation target material is switched by the flying focus technique. First of all, the user selects the patient imaging mode or calibration mode via the input unit 41. In the patient imaging mode, the X-ray controller 61 controls the magnetic field adjuster 67 so as to form a focus on the imaging target 773. More specifically, the magnetic field adjuster 67 adjusts the voltage value of the voltage to be applied to the magnetic field generator 75 so as to make the thermal electrons emitted from the filament 731 collide with the imaging target 773. In the patient imaging mode, the anode 77 is rotated about the anode rotation axis RA to prevent a deterioration in the imaging target 773 caused by the collision of thermal electrons. Note that when the X-rays generated in the patient imaging mode are allowed to include characteristic X-rays originating from the calibration target in addition to characteristic X-rays originating from the imaging target 773, a focus may be formed astride both the imaging target 773 and the calibration target.

In the calibration mode, the X-ray controller 61 controls the magnetic field adjuster 67 to generate X-rays from a material for calibration. Calibration may be executed at an arbitrary frequency. For example, calibration may be performed every night or every week. It is possible to arbitrarily select materials for calibration from the imaging target 773 and the plurality of calibration targets 775-1 and 775-2. At least two types of materials for calibration are selected. Selecting more types of materials can improve the calibration accuracy. For the sake of concreteness, assume that the imaging target 773, the first calibration target 775-1, and the second calibration target 775-2 have been selected. Note that materials for calibration may be selected by the user via the input unit 41 or may be set in advance.

In the calibration mode, the X-ray controller 61 controls the magnetic field adjuster 67 to sequentially form a focus on the imaging target 773, the first calibration target 775-1, and the second calibration target 775-2 at predetermined time intervals. More specifically, the magnetic field adjuster 67 adjusts the voltage value of a voltage to the magnetic field generator 75 so as to continuously collide thermal electrons with the imaging target 773 over the first acquisition period. When thermal electrons collide with the imaging target 773, the imaging target 773 generates X-rays. The generated X-rays have the energy component of a characteristic X-ray unique to the element forming the imaging target 773. The photon counting CT detector 15 detects X-rays originating from the imaging target 773, and acquires count data concerning the X-rays originating from the imaging target 773. After the first acquisition period, the magnetic field adjuster 67 adjusts the voltage value of a voltage to the magnetic field generator 75 so as to continuously collide thermal electrons with the first calibration target 775-1 over the second acquisition period. When thermal electrons collide with the first calibration target 775-1, the first calibration target 775-1 generates X-rays. The generated X-rays have the energy component of a characteristic X-ray unique to the element forming the first calibration target 775-1. The photon counting CT detector 15 detects X-rays originating from the first calibration target 775-1, and acquires count data concerning the X-rays originating from the first calibration target 775-1.

After the second acquisition period, the magnetic field adjuster 67 adjusts the voltage value of a voltage to the magnetic field generator 75 so as to continuously collide thermal electrons with the second calibration target 775-2 over the third acquisition period. When thermal electrons collide with the second calibration target 775-2, the second calibration target 775-2 generates X-rays. The generated X-rays have the energy component of a characteristic X-ray unique to the element forming the second calibration target 775-2. The photon counting CT detector 15 detects X-rays originating from the second calibration target 775-2, and acquires count data concerning the X-rays originating from the second calibration target 775-2. Each acquisition period may be set to a time that allows the acquisition of count data of a data amount sufficient to generate a histogram (to be described later).

According to the above description, the magnetic field adjuster 67 is controlled to sequentially form a focus on the imaging target 773, the first calibration target 775-1, and the second calibration target 775-2 at predetermined time intervals. However, this embodiment is not limited to this. That is, when the photon counting CT detector 15 has an energy resolution that can identify a characteristic X-ray unique to the imaging target 773, a characteristic X-ray unique to the first calibration target 775-1, and a characteristic X-ray unique to the second calibration target 775-2, the magnetic field adjuster 67 may be controlled to form a focus astride the imaging target 773, the first calibration target 775-1, and the second calibration target 775-2. In this case, the imaging target 773, the first calibration target 775-1, and the second calibration target 775-2 almost simultaneously generate a plurality of characteristic X-rays.

In the calibration mode, it is preferable to irradiate not only the central portion of the detection surface of the photon counting CT detector 15 but also the peripheral portion of the center portion with strong X-rays. In the calibration mode, a wedge filter is preferably retracted from the X-ray irradiation field.

Calibration processing by the calibration unit 35 will be described next. FIG. 7 is a graph schematically showing histograms Hi of X-ray photons detected by the photon counting CT detector 15. As exemplarily shown in FIG. 7, assume that a first histogram Hi-1 is a histogram concerning X-ray photons originating from the imaging target 773, a second histogram Hi-2 is a histogram concerning X-ray photons originating from the first calibration target 775-1, and a third histogram Hi-3 is a histogram concerning X-ray photons originating from the second calibration target 775-2. The calibration unit 35 generates each histogram Hi based on the count data acquired by the photon counting CT detector 15 in the calibration mode. More specifically, the calibration unit 35 generates each histogram Hi by analyzing the count data acquired in the calibration mode and plotting a count (incidence event count) for each energy bin (ADU). ADU is sometimes expressed as a channel.

Upon generating the histograms Hi-1, Hi-2, and Hi-3, the calibration unit 35 decides the relationship between the photon energies and the central channels based on the histograms Hi-1, Hi-2, and Hi-3. More specifically, first of all, the calibration unit 35 specifies ADU values Ch1, Ch2, and Ch3 of vertices P1, P2, and P3 of the histograms Hi-1, Hi-2, and Hi-3. The vertices P1, P2, and P3 of the respective histograms correspond to characteristic X-rays, typically, K emission lines. The histogram of X-rays including a characteristic X-ray typically has a sharp line structure originating from a K emission line. It is therefore possible to easily detect the vertices P1, P2, and P3 of the histograms by known numeral analysis or image processing. Note that the ADU values Ch1, Ch2, and Ch3 of the vertices P1, P2, and P3 are also called central channels.

Upon specifying the central channels Ch1, Ch2, and Ch3 of the respective histograms, the calibration unit 35 decides the relationship between the photon energies and the central channels. FIG. 8 is a graph showing the relationship between photon energies and central channels. Referring to FIG. 8, the ordinate is defined as the ADU value, and the abscissa is defined as the photon energy. As shown in FIG. 8, the calibration unit 35 plots the vertices P1, P2, and P3 of the respective histograms on the graph of FIG. 8. Note that the vertices P1, P2, and P3 of the respective histograms correspond to characteristic X-rays unique to the elements of the X-ray source materials. The photon energies of characteristic X-rays originating from the elements are experimentally or empirically known. Photon energies E1, E2, and E3 at the vertices P1, P2, and P3 of the histograms are known. Upon plotting the vertices P1, P2, and P3, the calibration unit 35 calculates a straight line LC fitting the vertices P1, P2, and P3. The straight line LC represents a relational expression between the photon energies and the central channels. In other words, the straight line LC represents a relational expression between the photon energies and ideal energy bins (ADU values) of X-ray photons having the photon energies.

Upon deciding the relational expression between the photon energies and the central channels, the calibration unit 35 calibrates the gain of the variable gain amplifier 53 in accordance with the relational expression. For example, when the photon counting CT detector 15 detects an X-ray photon having a photon energy Ex at an arbitrary point Px on the relational expression LC in FIG. 8, the calibration unit 35 calculates the gain (amplification ratio) with which an electrical signal originating from the X-ray photon has a peak value belonging to an energy bin (ADU value) Chx. The calibration unit 35 sets the calculated gain as the gain of the variable gain amplifier 53. Note that the arbitrary point Px may be any point including the points P1, P2, and P3 as long as it is located on the straight line LC.

In this manner, the calibration unit 35 according to this embodiment calibrates the gain of the photon counting CT detector 15 by using count data originating from a plurality of characteristic X-rays concerning different energy bins. As compared with the related art which uses count data originating from a single characteristic X-ray, the calibration unit 35 according to the embodiment can accurately calibrate the gain of the photon counting CT detector 15. This can improve the accuracy and quantitativeness of material discrimination in photon counting CT.

This is the end of the description about calibration processing by the calibration unit 35.

In the above description, it is assumed that the calibration unit 35 calibrates the gain of the photon counting CT detector 15 by using count data from the photon counting CT detector 15. However, this embodiment is not limited to this. For example, the calibration unit 35 calibrates the gain of the photon counting CT detector 15 by using an electrical signal from the variable gain amplifier 53. In this case, the output device 59 A/D-converts an electrical signal from the variable gain amplifier 53, and transmits the A/D-converted electrical signal to the console 30.

In the above description, the calibration target 775 is formed into an annular shape. However, the shape of the calibration target 775 is not limited town annular shape, and may be an arbitrary shape such as a rectangular shape. In this case, the calibration target 775 is preferably arranged in a local region of the imaging target 773. In this case, in X-ray irradiation for calibration, the anode 77 need not rotate about the anode rotation axis RA. That is, the anode 77 is positioned at a stage prior to X-ray irradiation for calibration so as to superimpose the collision surface (focus) of thermal electrons from the filament 731 on the calibration target 775. In addition, when a plurality of calibration targets 775 are arranged in local regions of the imaging target 773, the arraying direction of the plurality of calibration targets 775 is not limited to the radial direction of the anode. For example, these targets may be arrayed in a non-radial direction such as the circumferential direction of the anode 77.

In addition, in the above description, the gain of the photon counting CT detector 15 is calibrated by calibrating the gain of the variable gain amplifier 53. However, this embodiment is not limited to this. For example, the gain of the photon counting CT detector 15 may be calibrated by calibrating the gain of the preamplifier 51. In addition, the gain of the photon counting CT detector 15 may be calibrated by calibrating the gain of each detector element included in the X-ray detector 151. In this case, the gain of the photon counting CT detector 15 is calibrated by adjusting the voltage value of the voltage to be applied to each detector element. In addition, if the signal processing circuit 153 includes another constituent element (e.g., a waveform shaper) (not shown), the gain of the photon counting CT detector 15 may be calibrated by calibrating the gain of the constituent element.

In the above description, the calibration unit 35 is provided in the console 30. However, this embodiment is not limited to this. For example, the calibration unit 35 may be provided in the photon counting CT detector 15.

(Modification 1)

In the above embodiment, the X-ray controller 61 controls the magnetic field adjuster 67 to change the focus by deflecting the path of thermal electrons. However, this embodiment is not limited to this. The X-ray controller 61 according to modification 1 controls the focus adjuster 69 to change the focus by changing the size of the focus. Modification 1 of this embodiment will be described below. The same reference numerals as in the first embodiment denote constituent elements having almost the same functions in the following description, and a repetitive description will be made only when required.

In the patient imaging mode, the X-ray controller 61 according to modification 1 controls the focus adjuster 69 to form a focus on at least the imaging target 773. More specifically, the focus adjuster 69 adjusts the voltage value of the electrode voltage to be applied to the focusing electrode 733 so as to make the thermal electrons emitted from the filament 731 collide with at least the imaging target 773. Note that when X-rays generated in the patient imaging mode may include a characteristic X-ray originating from the calibration target 775 in addition to a characteristic X-ray originating from the imaging target 773, a focus may be formed astride both the imaging target 773 and the calibration target 775. In the calibration mode, the X-ray controller 61 controls the focus adjuster 69 to form a focus on at least two types of calibration materials. More specifically, the focus adjuster 69 adjusts the voltage value of the focusing electrode voltage to be applied to the focusing electrode 733 so as to make the thermal electrons emitted from the filament 731 collide with at least two types of calibration materials.

As described above, according to modification 1, since there is no need to provide the magnetic field adjuster 67 and the magnetic field generator 75, it is possible to implement the X-ray source apparatus 13 which can generate a plurality of characteristic X-rays having different energies at a lower cost than in the above embodiment.

(Modification 2)

In the above embodiment, the plurality of calibration targets 775 are arranged side by side on the imaging target 773. However, this embodiment is not limited to this. The plurality of calibration targets 775 according to modification 2 are overlaid on each other on the imaging target 773. Modification 2 of this embodiment will be described below. The same reference numerals as in the above embodiment denote constituent elements having almost the same functions in the following description, and a repetitive description will be made only when required.

Figure 9:
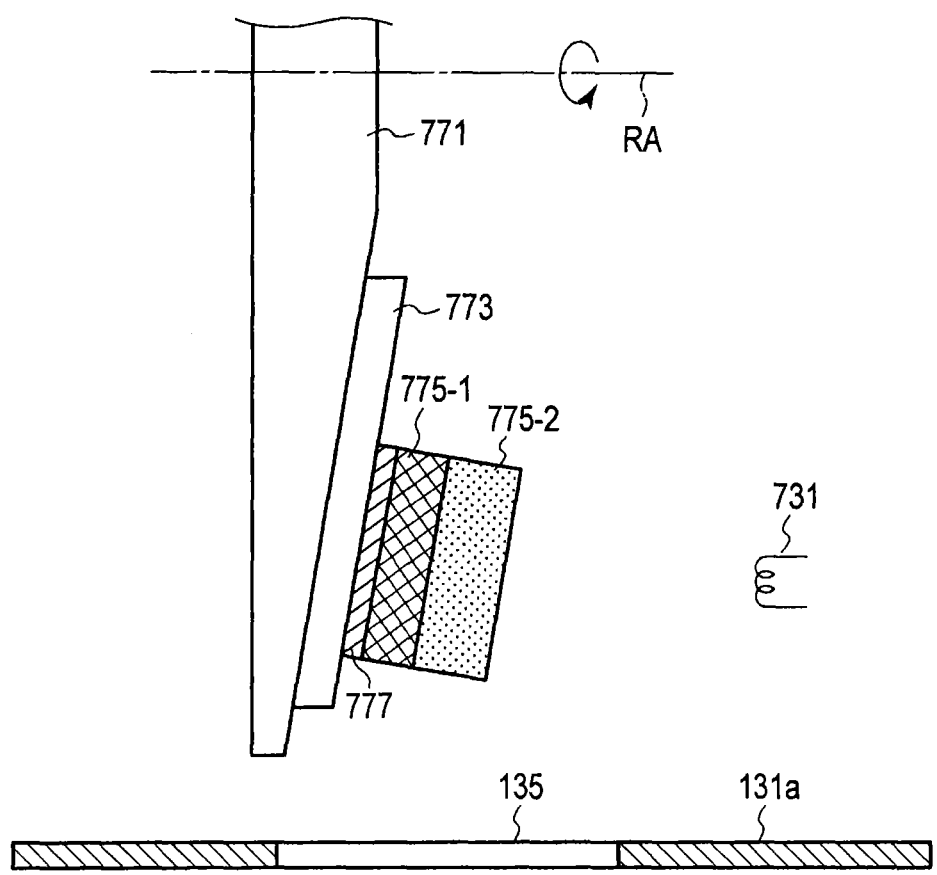
FIG. 9 is a view schematically showing the interior of an X-ray source apparatus according to modification 2.

FIG. 9 is a view schematically showing the interior of the X-ray source apparatus 13 according to modification 2. As shown in FIG. 9, the plurality of calibration targets 775 according to modification 2 are overlaid on each other on the imaging target 773. Referring to FIG. 9, for example, the calibration target 775-1 is mounted on the surface of the imaging target 773, and the calibration target 775-2 is mounted on the surface of the calibration target 775-1. The heat insulator 777 is interposed between the imaging target 773 and the calibration target 775-1. Note that the surface of the imaging target 773 squarely faces the filament 731 of the imaging target 773. The surface of the calibration target 775-1 is located on the opposite side to the connecting surface with the imaging target 773. The higher the voltage value of a tube voltage, the deeper thermal electrons enter a material. In addition, the larger the atomic number of an element, the higher the probability of interaction with thermal electrons. For this reason, the plurality of calibration targets 775-1 and 775-2 are sequentially arranged from the near side to the far side of the imaging target 773 in descending order of atomic number. In the case in FIG. 9, the calibration target 775-1 near the imaging target 773 has a larger atomic number than the calibration target 775-2 far from the imaging target 773.

X-ray irradiation from the X-ray source 131 performed under the control of the X-ray controller 61 according to modification 2 will be described next.

In the calibration mode, the X-ray controller 61 controls the high voltage generator 63 to generate X-rays from a calibration material. The X-ray controller 61 controls the high voltage generator 63 to sequentially apply a plurality of calibration tube voltages so as to sequentially generate X-rays from calibration materials. Each tube voltage for calibration is set to a voltage value that enables thermal electrons to reach a calibration material. Each of a plurality of tube voltages for calibration is set to a voltage value in accordance with the element of a material corresponding to the tube voltage for calibration. Materials for calibration can be arbitrarily selected from the imaging target 773 and the plurality of calibration targets 775. For the sake of concreteness, assume that the first calibration target 775-1 and the second calibration target 775-2 have been selected.

FIG. 10 is a view for explaining an example of the operation of the X-ray controller 61 according to modification 2, and schematically showing an example of generating X-rays from the first calibration target 775-1. When generating X-rays from the first calibration target 775-1, the X-ray controller 61 applies a first tube voltage kV1 between the cathode 73 and the anode 77. The first tube voltage kV1 is set to a voltage value that enables thermal electrons to reach the calibration target 775-1 upon being transmitted through the calibration target 775-2. When the thermal electrons collide with the element in the calibration target 775-2, the calibration target 775-2 generates X-rays.

Note that thermal electrons sometimes collide with the element in the calibration target 775-2 under the application of the first tube voltage kV1. In this case, the calibration target 775-1 generates X-rays. That is, the X-rays generated by the anode 77 under the application of the first tube voltage kV1 contain energy components originating from the calibration target 775-2 and energy components originating from the calibration target 775-1. In order to remove the unnecessary energy components, a plurality of X-ray filters corresponding to the plurality of calibration targets 775-1 and 775-2, respectively. The X-ray filter corresponding to the calibration target is formed from the similar type of element as that in the corresponding calibration target. More specifically, the similar type of X-ray filter is formed from the element with the atomic number within the range of ±10 centering the atomic number of corresponding calibration target. The X-ray filter corresponding to the calibration target used for calibration is set to the window 135. For example, in the case of the second tube voltage kV2, the X-ray filter corresponding to the calibration target 775-2 is set to the window 135. Or again, in the case of the first tube voltage kV1, The X-ray filter corresponding to the calibration target 775-1 is set to the window 135. In this case, the energy components originating from the calibration target 775-2 are removed from the X-rays passing through the window 135. As a result, the energy components originating from the calibration target 775-1 are dominant in the X-rays. In other words, the X-ray filter monochromizes the X-rays generated by the X-ray source 131. This can increase the S/N ratio of characteristic X-rays. For example, the first calibration target 775-1 is preferably made of lead, and the second calibration target 775-2 is preferably made of tin. The window 135 is provided with an X-ray filter formed from the similar type of element as that of the calibration target 775-1 located closer to the imaging target 773. If, for example, the first calibration target 775-1 is made of lead and the second calibration target 775-2 is made of tin, the window 135 is provided with an X-ray filter formed from the lead or the similar type of elements. The photon counting CT detector 15 detects the X-rays irradiated from the X-ray source apparatus 13. The detected X-rays contain a characteristic X-ray unique to the element contained in the calibration target 775-1 but does not contain any characteristic X-ray unique to the element contained in the calibration target 775-2.

Note that if the photon counting CT detector 15 has an energy resolution that can individually identify a characteristic X-ray unique to the element in the calibration target 775-2 and a characteristic X-ray unique to the element in the calibration target 775-1, no X-ray filter may be provided for the window 135.

Figure 11:
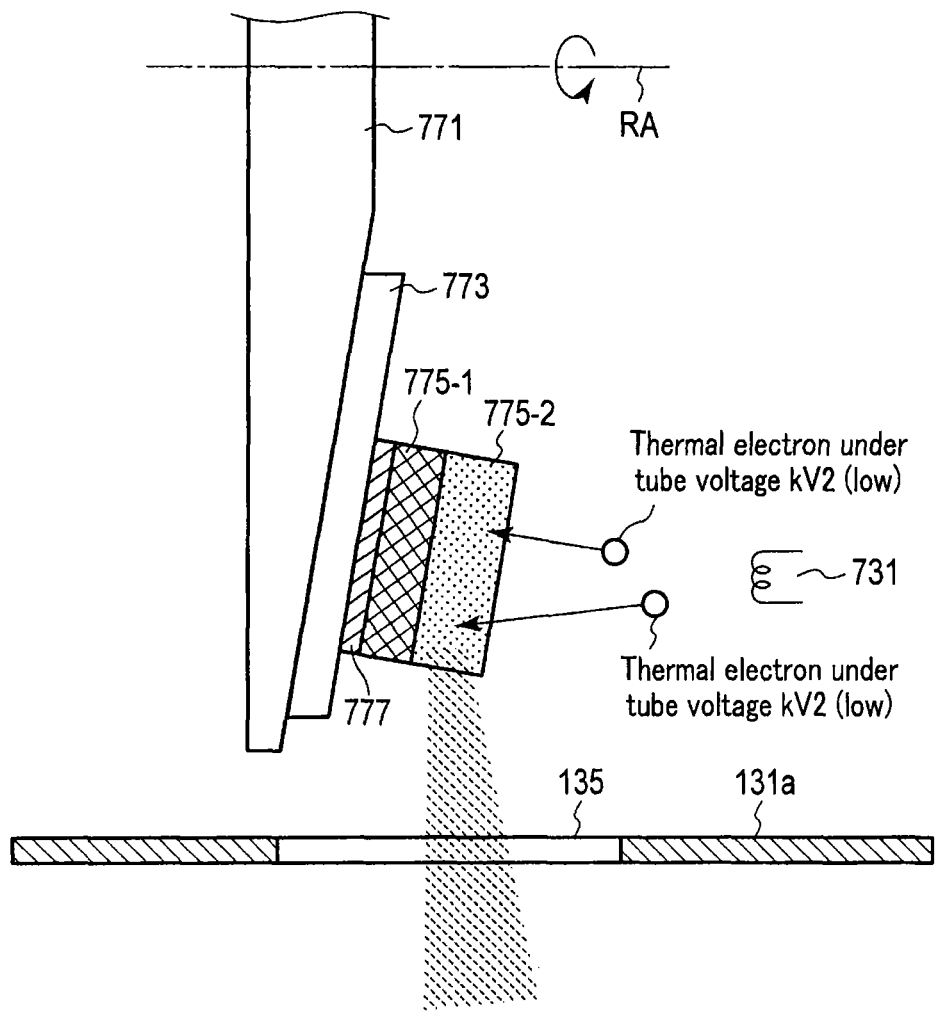
FIG. 11 is a view for explaining an example of the operation of the X-ray controller according to modification 2, and schematically showing an example of generating X-rays from the second calibration target.

FIG. 11 is a view for explaining an example of the operation of the X-ray controller 61 according to modification 2, and schematically showing an example of generating X-rays from the second calibration target 775-2. When generating X-rays from the second calibration target 775-2, the X-ray controller 61 applies a second tube voltage kV2 between the cathode 73 and the anode 77. The second tube voltage kV2 is set to a voltage value low enough not to be transmitted through the calibration target 775-2. The second tube voltage kV2 is lower in voltage value than the first tube voltage kV1. When thermal electrons collide with the element in the calibration target 775-2, the calibration target 775-2 generates X-rays. Note that there is only a negligible probability that thermal electrons are transmitted through the calibration target 775-1 under the application of the second tube voltage kV2. The window 135 is provided with an X-ray filter formed from the similar type of element as that of the calibration target 775-2. If, for example, the first calibration target 775-1 is made of lead and the second calibration target 775-2 is made of tin, the window 135 is provided with an X-ray filter formed from the tin or the similar type of elements. The photon counting CT detector 15 detects the X-rays irradiated from the X-ray source apparatus 13. The detected X-rays contain a characteristic X-ray unique to the element contained in the calibration target 775-2 but does not contain any characteristic X-ray unique to the element contained in the calibration target 775-1.

According to the above description, the X-ray controller 61 sequentially applies the first and second tube voltages to allow the photon counting CT detector 15 to acquire count data concerning a characteristic X-ray unique to the calibration target 775-1 and a characteristic X-ray unique to the calibration target 775-2. However, this embodiment is not limited to this. If the photon counting CT detector 15 has an energy resolution that can individually identify a characteristic X-ray unique to the element in the calibration target 775-2 and a characteristic X-ray unique to the element in the calibration target 775-1, the X-ray controller 61 may apply only the first tube voltage between the cathode 73 and the anode 77. This makes it possible for the photon counting CT detector 15 to acquire count data concerning characteristic X-rays originating from the calibration target 775-2 and characteristic X-rays originating from the calibration target 775-1. In this case, the window 135 need not be provided with any X-ray filter formed from the similar type of element as that of the calibration target 775-1.

In the patient imaging mode, the X-ray controller 61 according to modification 2 controls the high voltage generator 63 to generate X-rays from the imaging target 773. More specifically, the high voltage generator 63 adjusts the voltage value of a tube voltage so as to make the thermal electrons emitted from the filament 731 reach the imaging target 773. If energy components originating from the calibration target 775-2 and the calibration target 775-1 are not necessary, the window 135 is preferably provided with an X-ray filter formed from the similar type of element as that of the imaging target 773.

As described above, according to modification 2, it is possible to generate a plurality of characteristic X-rays having different energies by adjusting a tube voltage value. This obviates the necessity to adjust a focus by, for example, changing the focus size or deflecting the path of thermal electrons. It is therefore possible to easily generate a plurality of characteristic X-rays having different energies at a low cost as compared with the above embodiment.

(Modification 3)

According to the above embodiment, the X-ray source apparatus 13 is equipped with the signal filament 731. However, this embodiment is not limited to this. The X-ray source apparatus 13 according to modification 3 is equipped with a plurality of filaments for switching between X-ray sources. Modification 3 of the embodiment will be described below. The same reference numerals as in the above embodiment denote constituent elements having almost the same functions in the following description, and a repetitive description will be made only when required.

FIG. 12 is a block diagram schematically showing the arrangement of the X-ray source apparatus 13 according to modification 3. As shown in FIG. 12, the X-ray source apparatus 13 shown in FIG. 1 according to modification 3 includes the X-ray source 131 and the high voltage generation unit 133. The high voltage generation unit 133 includes the X-ray controller 61, the high voltage generator 63, the filament current adjuster 65, the focus adjuster 69, and a switch 81.

The X-ray source apparatus 13 according to modification 3 has a plurality of cathodes in the housing 71a. For example, the housing 71a is equipped with three cathodes 73-1, 73-2, and 73-3, as shown in FIG. 12. For example, the number of cathodes provided is equal to the total number of imaging targets 773 and calibration targets. As shown in FIGS. 5 and 6, the plurality of calibration targets 775-1 and 775-2 are arranged side by side on the imaging target 773. Each of the plurality of cathodes includes the filament 731 and the focusing electrode 733. A plurality of filaments 731 are connected to the switch 81. Each filament 731 is positioned for thermal electrons colliding with a collision target material. A plurality of focusing electrodes 733 are connected to the focus adjuster 69.

The switch 81 is configured to switch connection between the plurality of filaments 731 and the high voltage generator 63. The switch 81 connects one of the plurality of connection target filaments 731 which is a connection target to the high voltage generator 63 so as to energize the connection target filament 731 under the control of the X-ray controller 61. In the patient imaging mode, as the connection target filament 731, the filament 731 corresponding to the imaging target 773 is set. In the calibration mode, as the connection target filament 731, the filament 731 corresponding to a material used for calibration is set. As materials used for calibration, at least two types of materials are selected from the imaging target 773 and the plurality of calibration targets 775-1 and 775-2.

The focus adjuster 69 applies a focusing electrode voltage to the focusing electrode 733 corresponding to the connection target filament 731 under the control of the X-ray controller 61. Note that in order to avoid complicated control, the X-ray controller 61 may always apply focusing electrode voltages to the plurality of focusing electrodes 733 at the time of X-ray irradiation.

X-ray irradiation to be performed under the control of the X-ray controller 61 according to modification 3 will be described next. FIG. 13 is a view for explaining an example of the operation of the X-ray controller 61 according to modification 3. As shown in FIG. 13, the plurality of calibration targets 775-1 and 775-2 are arranged on the imaging target 773. The heat insulators 777 are interposed between the imaging target 773 and the calibration target 775-1 and between the imaging target 773 and the calibration target 775-2. A filament 731-1 is positioned to form a focus on the imaging target 773. A filament 731-2 is positioned to form a focus on the first calibration target 775-1. A filament 731-3 is positioned to form a focus on the second calibration target 775-2.

In the patient imaging mode, the X-ray controller 61 according to modification 3 controls the switch 81 to energize the filament 731-1 corresponding to the imaging target 773. More specifically, the switch 81 connects the filament 731-1 corresponding to the imaging target 773 to the high voltage generator 63 to energize the filament 731-1. With this operation, the filament 731-1 generates heat and emits thermal electrons. The emitted thermal electrons collide with the element in the imaging target 773. The imaging target 773 then generates X-rays.

In the calibration mode, the X-ray controller 61 controls the switch 81 to sequentially energize at least the two filaments 731 corresponding to at least two types of materials for calibration. For the sake of concreteness, assume that the materials for calibration are the imaging target 773, the first calibration target 775-1, and the second calibration target 775-2. In the first acquisition period in the calibration mode, first of all, the X-ray controller 61 controls the switch 81 to energize the filament 731-1 corresponding to the imaging target 773. The switch 81 connects the filament 731-1 corresponding to the imaging target 773 to the high voltage generator 63 under the control of the X-ray controller 61. With this operation, the imaging target 773 generates X-rays. The photon counting CT detector 15 detects the generated X-rays originating from the imaging target 773, and acquires count data concerning the detected X-rays. In the second acquisition period after the first acquisition period, the X-ray controller 61 controls the switch 81 to energize the filament 731-2 corresponding to the first calibration target 775-1. The switch 81 connects the filament 731-2 to the high voltage generator 63 under the control of the X-ray controller 61. With this operation, the first calibration target 775-1 generates X-rays. The photon counting CT detector 15 detects the generated X-rays originating from the first calibration target 775-1, and acquires count data concerning the detected X-rays. In the third acquisition period after the second acquisition period, the X-ray controller 61 controls the switch 81 to energize the filament 731-3 corresponding to the second calibration target 775-2. The switch 81 connects the filament 731-3 to the high voltage generator 63 under the control of the X-ray controller 61. With this operation, the second calibration target 775-2 generates X-rays. The photon counting CT detector 15 detects the generated X-rays originating from the second calibration target 775-2, and acquires count data concerning the detected X-rays.

Note that even in modification 3, if the energy resolution of the photon counting CT detector 15 is low, an X-ray filter may be provided for the window 135. For example, to collide thermal electrons with the calibration target 775-1, the window 135 is preferably provided with an X-ray filter formed from the similar type of element as that in the calibration target 775-1. To collide thermal electrons with the calibration target 775-2, the window 135 is preferably provided with an X-ray filter formed from the similar type of element as that in the calibration target 775-2. Providing an X-ray filter for the window 135 can monochromize the X-rays generated by the X-ray source 131 via the X-ray filter, and hence can increase the S/N ratio of characteristic X-rays.

As described above, according to modification 3, filaments are respectively provided for a plurality of X-ray sources. This obviates the necessity to perform complicated focus control such as changing a focus size or deflecting the path of thermal electrons.

(Modification 4)

In the above embodiment, the gain of the photon counting CT detector 15 is calibrated based on the relationship between the photon energies of a plurality of characteristic X-rays and outputs from the photon counting CT detector 15. However, this embodiment is not limited to this. For example, the signal processing circuit 153 may correct outputs (count data) from the photon counting CT detector 15 based on the relationship between the photon energies of a plurality of characteristic X-rays and outputs from the photon counting CT detector 15. For example, as described, in the calibration mode, the calibration unit 35 generates a histogram of X-ray photons originating from each target based on the count data acquired by the photon counting CT detector 15, and decides the relationship between the photon energies and the central channels based on the generated histograms. The decided relationship is supplied to the signal processing circuit 153. The signal processing circuit 153 corrects the count data acquired in the patient imaging mode in accordance with the relationship. For example, the signal processing circuit 153 shifts the ADU value at each data point of the count data acquired in the patient imaging mode in accordance with the relationship. This makes it possible to suppress a deterioration in count data caused by mismatching between a photon energy and an output from the photon counting CT detector 15 without calibrating the gain of the photon counting CT detector 15. Note that the reconstruction unit 33 may correct count data in accordance with the relationship.

As described above, this embodiment provides a photon counting CT apparatus which can accurately calibrate the gain of the detector.

Note that according to the above description, the photon counting CT apparatus is a so-called third-generation apparatus. That is, the photon counting CT apparatus is a rotate/rotate-type apparatus configured to make the X-ray source and the photon counting CT detector integrally rotate around the subject S. However, the photon counting CT apparatus according to this embodiment is not limited to this. For example, the photon counting CT apparatus may be a stationary/rotate-type apparatus in which many detector pixels arrayed in the form of a ring are fixed, and only the X-ray source rotates around the subject S.

The word "processor" used in the above description indicates, for example, a dedicated or general-purpose processor, circuit (circuitry), processing circuit (circuitry), operation circuit (circuitry), arithmetic circuit (circuitry), ASIC (Application Specific Integrated Circuit), SPLD (Simple Programmable, Logic Device), CPLD (Complex Programmable Logic Device), or FPGA (Field Programmable Gate Array). In addition, each constituent element (each processing unit) of this embodiment may be implemented by a plurality of processors instead of a single processor. Furthermore, a plurality of constituent elements (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon-counting CT apparatus, comprising:
   an X-ray source including a cathode configured to generate electrons and an anode having a plurality of targets configured to generate a plurality of characteristic X-rays having different energies;
   a photon-counting CT detector configured to detect X-ray photons of the plurality of characteristic X-rays generated by the X-ray source; and
   a calibration circuit configured to calibrate a gain of the photon-counting CT detector based on a correspondence relationship between photon energies of the plurality of characteristic X-rays and outputs from the photon-counting CT detector.

2. The photon-counting CT apparatus of claim 1, wherein the anode further includes a base provided to rotate, and
   the plurality of targets include an imaging target provided on the base and a plurality of calibration targets provided on the imaging target and configured to generate the plurality of characteristic X-rays.

3. The photon-counting CT apparatus of claim 2, wherein the anode further includes a heat insulator configured to insulate heat from the imaging target is interposed between the imaging target and the plurality of calibration targets.

4. The photon-counting CT apparatus of claim 2, wherein the plurality of calibration targets are arranged side by side on the imaging target.

5. The photon-counting CT apparatus of claim 4, wherein the plurality of calibration targets are arranged side by side in a radial direction of the imaging target.

6. The photon-counting CT apparatus of claim 4, further comprising:
   a magnetic field generator configured to generate a magnetic field to deflect a path of an electron beam generated by the cathode; and
   a controller configured to control the magnetic field generator to collide an electron beam emitted from the cathode with the imaging target in a patient imaging mode and an electron beam emitted from the cathode with a material, of the imaging target and the plurality of calibration targets, which is used for calibration in a calibration mode.

7. The photon-counting CT apparatus of claim 4, further comprising:
   a focusing device configured to focus an electron beam emitted from the cathode; and
   a controller configured to switch a focus size on the anode in accordance with a patient imaging mode and a calibration mode.

8. The photon-counting CT apparatus of claim 4, wherein the cathode comprises a plurality of filaments, and
   the photon-counting CT apparatus further comprises a high voltage generator configured to generate a high voltage to be applied to the X-ray source,
   a switch configured to switch connection between the plurality of filaments and the high voltage generator, and
   a controller configured to conduct a filament, of the plurality of filaments, which corresponds to the imaging target in a patient imaging mode, and conduct filaments, of the plurality of filaments, which correspond to the imaging target and a calibration target, of the plurality of calibration targets, which is used for calibration in a calibration mode.

9. The photon-counting CT apparatus of claim 2, wherein the plurality of calibration targets are overlaid on each other on the imaging target.

10. The photon-counting CT apparatus of claim 9, wherein the plurality of calibration targets are sequentially overlaid on each other on the surface of the imaging target in descending order of atomic numbers.

11. The photon-counting CT apparatus of claim 10, wherein the X-ray source further comprises an X-ray tube accommodating the base, the imaging target, and the plurality of calibration targets, and an X-ray tube container having a window formed therein and configured to accommodate the X-ray tube.

12. The photon-counting CT apparatus of claim 9, further comprising:

a high voltage generator configured to generate a high voltage to be applied between the cathode and the anode; and a controller configured to generate a voltage value that enables an electron emitted from the cathode to reach the imaging target in a patient imaging mode and generate a voltage value that enables the electron to reach a calibration target, of the plurality of calibration targets, which is used for calibration in a calibration mode.

13. The photon-counting CT apparatus of claim 1, wherein the photon-counting CT detector further comprises an X-ray detector configured to detect an X-ray photon of the plurality of characteristic X-rays from the X-ray source and a signal processing circuit configured to process an output signal from the X-ray detector, the signal processing circuit comprises a variable amplifier configured to amplify an output signal from the detector with a variable gain, and the calibration circuit adjusts the variable gain based on the correspondence relationship.

14. The photon-counting CT apparatus of claim 13, further comprising a reconstruction circuit, wherein the signal processing circuit comprises a counting circuit configured to generate count data representing a count value of X-ray photons of the plurality of characteristic X-rays for each of a plurality of energy bins based on an output signal from the variable amplifier, and the reconstruction circuit reconstructs an image concerning a target energy bin of the plurality of energy bins based on count data concerning the target energy bin.

15. The photon-counting CT apparatus of claim 1, wherein the calibration circuit specifies outputs of at least two characteristic X-rays of the plurality of characteristic X-rays based on an output signal from the photon-counting CT detector, calculates a gain based on the specified outputs concerning the at least two characteristic X-rays and a known photon energy, and sets a gain of the photon-counting CT detector to the calculated gain.

16. A photon-counting CT apparatus, comprising:

an X-ray source including a cathode configured to generate electrons and an anode having a plurality of targets configured to generate a plurality of characteristic X-rays having different energies;

a photon-counting CT detector configured to detect X-ray photons of the plurality of characteristic X-rays generated by the X-ray source; and a calibration circuit configured to determine a correspondence relationship between photon energies of the plurality of characteristic X-rays and outputs from the photon-counting CT detector, wherein the photon-counting CT detector comprises an X-ray detector configured to detect an X-ray photon of the plurality of characteristic X-rays from the X-ray source and a signal processing circuit configured to generate count data based on the detected X-ray photon by the X-ray detector, and the signal processing circuit is configured to correct the count data based on the correspondence relationship.

* * * * *